United States Patent [19]

Keve et al.

[11] 4,419,359
[45] Dec. 6, 1983

[54] NITRO-SUBSTITUTED POLYCYCLIC DERIVATIVES USEFUL IN THE TREATMENT OF PSORIASIS

[75] Inventors: Tibor Keve; György Fekete; Csaba Lörincz, all of Budapest; Janos Galambos, Erd; Bela Zsadon, Budapest; Maria Zájer née Balázs, Budapest; Lilla Forgách, Budapest; Egon Kárpáti, Budapest; Arpád Király, Budapest; Gyóngyver Király née Soos, Budapest; Laszlo Szporny, Budapest; Béla Rosdy, Budapest, all of Hungary

[73] Assignee: Richter Gedeon Vegyeszeti Gyar RT, Budapest, Hungary

[21] Appl. No.: 345,631

[22] Filed: Feb. 4, 1982

[30] Foreign Application Priority Data

Feb. 11, 1981 [HU] Hungary .................. 323/81

[51] Int. Cl.$^3$ .................. A61K 31/435; C07D 461/00
[52] U.S. Cl. ........................................ 424/256; 546/51
[58] Field of Search ........................... 546/51; 424/256

[56] References Cited

U.S. PATENT DOCUMENTS 4,065,458 12/1977 Lorincz et al. .................. 424/256 X
4,108,996 8/1978 Lorincz et al. .................. 424/256
4,328,231 5/1982 Zajer nee Balazs et al. ....... 424/256

FOREIGN PATENT DOCUMENTS 2342980 11/1977 France .................. 424/256
2462909 2/1981 France .

OTHER PUBLICATIONS

Lorincz et al., Chemical Abstracts, vol. 82, 129279v, (1975).

Primary Examiner—Diana G. Rivers
Attorney, Agent, or Firm—Karl F. Ross; Herbert Dubno

[57] ABSTRACT

The present invention relates to the compounds of the Formulae 1a and 1b and pharmaceutically acceptable acid addition salts thereof.

The new 9-nitro-apovincaminol-3',4',5'-trimethoxybenzoate of the Formula 1a and the 11-nitro-apovincaminol-3',4',5'-trimethoxy-benzoate of the Formula 1b and pharmaceutically acceptable acid addition salts thereof can be prepared by nitrating the apovincaminol-3',4',5'-trimethoxy-benzoate of the Formula 11, if desired separating the mixture of the compounds of the Formulae 1a and 1b thus obtained into its components, if desired converting a compound of the Formula 1a or 1b thus obtained into pharmaceutically acceptable acid addition salts thereof.

The new compounds of the present invention can be used in therapy in the treatment of psoriasis.

10 Claims, No Drawings

NITRO-SUBSTITUTED POLYCYCLIC DERIVATIVES USEFUL IN THE TREATMENT OF PSORIASIS

The present invention relates to new nitro-substituted polycyclic derivatives, a process for the preparation thereof and pharmaceutical compositions containing the same.

According to an aspect to the present invention there are provided new components of the Formula Ia and Ib

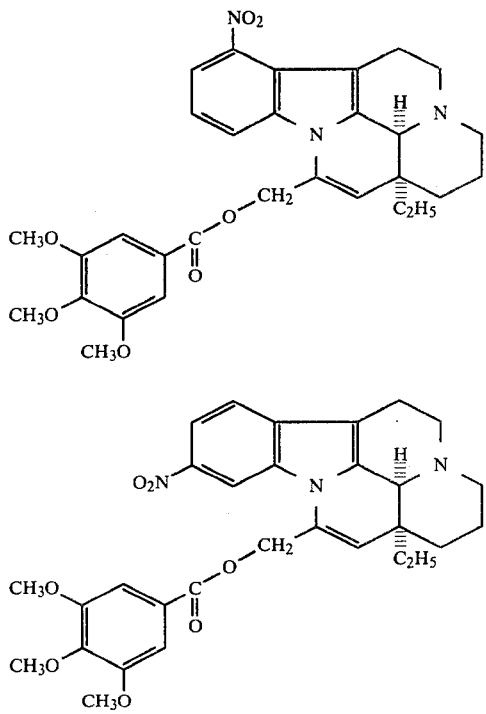

and pharmaceutically acceptable acid addition salts thereof.

The compound of the Formula Ia is the (—)-9-nitroapovincaminol-3',4',5'-trimethoxy-benzoate and the compound of the Formula Ib is the (—)-11-nitro-apovincaminol-3',4',5'-trimethoxy-benzoate.

The acid addition salts of the compounds of the Formulas Ia and Ib may be formed with inorganic or organic acids. From the salts formed with inorganic acids the hydrochlorides, sulfates and phosphates, while from the salts formed with organic acids the hydrogen tartarates, succinates, citrates and ascorbates are particularly useful.

It is known that the apovincaminol and its acetate exhibit an effect on the coronary artery (French Patent Specification No. 2 035 784). It is also known that the apovincaminol benzoate possesses general vasodilatory properties (Hungarian Patent Specification No. 166 476; CA 82, 129 279 v /1975) and the esters of apovincaminol formed with alkane carboxylic acid having 3–12 carbon atoms exhibit cerebral vasodilatory effect (Hungarian Patent Specification No. 171 662, the corresponding U.S. Pat. No. 4,108,996 and the BR German Federal Republic Patent Specification No. 26 32 118).

Thus all the known esters of apovincaminol exhibit vascotropic effects. On the other hand the new compound of the present invention inhibit the enzyme activity of phosphodiesterase and can be used first of all in the treatment of skin diseases, especially psoriasis.

The new compound of the Formula II

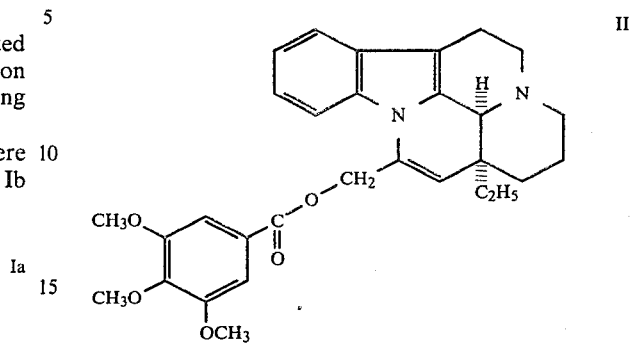

used as starting material and the process for the preparation thereof is claimed and described in our co-pending patent application. The preparation of the compound of the Formula II is described at the end of Example I, too.

Diseases attached to the pathological proliferation of the epidermis are relatively frequent and involve a few percents of the population. These diseases include psoriasis.

Since some of the skin diseases attached to pathological cell proliferation (e.g. psoriasis) do not occur on animals, the activity of the compounds against psoriasis can be made probable in animal tests only in an indirect manner.

Voorhees et al. [Arch. Derm. 104, 359–365 (1971)] have found that the pathological cell proliferation is accompanied by the decrease of the level of cyclic adenozine monophosphate (c-AMP). It is known that c-AMP is formed under the effect of adenyl-cyclase and decomposed by phosphodiesterase. Voorhees succeeded in influencing the psoriases by agents which stimulate the function of adenyl cyclase (such as nor-epinephrine) or inhibit the function of phosphodiesterase (e.g. papaverine).

By planning our model experiment test we have started from the presumption that the statement of Voorhees in relevant to the contrary as well. Thus if it can be proven that a compound inhibits the function of phosphodiesterase this makes it probable in an indirect way that the said compound is suitable for the treatment of skin diseases attached to the pathological cell proliferation.

Later this presumption turned out to be true: compounds showing phosphodiesterase inhibiting activity in in vitro tests proved to be active in the treatment of psoriasis in clinical experiments as well.

Our model tests are carried out with the aid of phosphodiesterase isolated from animal body tissues (rat brain, bovine brain, bovine heart). The enzyme is isolated according to the method of J. Schröder and H. V. Richenberg [Biochem. Biophys. Acta 302, 50 (1973)], the isolated phosphodiesterase is purified by the method of J. G. Hardman and E. W. Sutherland [J. Biol. Chem. 240, 3704 (1965)] and finally the activity of the purified enzyme is measured according to the radioisotope method of G. Pöch in the presence of an excess of tritiated c-AMP (10.1 millimoles of c-AMP substrate, from which the 3H-c-AMP is 2.59 K Bq) in an incubation system at first without inhibitory agent, and thereafter in the presence of 9-nitro- or 11-nitro-apovincaminol-3',4',5'-trimethoxy benzoate, respectively, as inhibitor after an incubation period of 20 minutes [N. S. Arch. Pharmacol. 268, 272 (1971)]. From the test compound a 1 millimolar stock solution is prepared and to the incubated enzyme preparation various amounts are added with the aid of the said stock solution so that the concentration of the test compound in the incubated sample should correspond to $5\times10^{-7}$, $1\times10^{-6}$, $5\times10^{-6}$, $1\times10^{-5}$, $5\times10^{-5}$ and $10^{-4}$ mole/liter, respectively. The aqueous solution of the reference compound (papaverine) is added to the enzyme prepared a similar manner.

The activity of the control (enzyme solution containing inhibitor) is taken as 100% and the activity of the solutions containing the 9-nitro- or 11-nitro-apovincaminol-3',4',5'-trimethoxy-benzoate and the papaverine is expressed in the percentage of the control. The results measured on the enzyme isolated from rat brain are as follows:

| Test compound (enzyme inhibitor) | Concentration of the test compound, mole/liter | | |
|---|---|---|---|
| | $5\times10^{-6}$ | $1\times10^{-5}$ | $5\times10^{-5}$ |
| | Effect of the enzyme activity, % of the control | | |
| (−)-11-nitro-apovincaminol-3',4',5'-trimethoxy-benzoate.HCl | 53.6 | 44.4 | 37.3 |
| (−)-9-nitro-apovincaminol-3',4',5'-trimethoxy-benzoate.HCl | 62.9 | 61.6 | 37.7 |
| Papaverine.HCl | 91.2 | 89.7 | 60.5 |

The results on enzyme isolated from bovine heart are measured in a similar manner. By using the results obtained, the enzyme activity is plotted against the logarithm of the enzyme inhibitor concentration (expressed in μmoles). The concentration of the enzyme inhibitor which decreases the enzyme activity by 50% ($I_{50}$) is read off the curve. The results obtained are summarized in the following Table.

| Test compound | $I_{50}$ values, in μmoles on phosphodiesterase enzyme isolated from | |
|---|---|---|
| | bovine heart | rat brain |
| (−)-11-nitro-apovincaminol-3',4',5'-trimethoxy-benzoate-HCl | 1 | 1 |
| (−)-9-nitro-apovincaminol-3',4',5'-trimethoxy-benzoate-HCl | 1 | 15 |
| Papaverine.HCl | 50 | 70 |

It appears from the above Table that on enzymes isolated from bovine heart and rat brain the new compounds of the present invention are 50 and 4.5–9 times, respectively, more active than the papaverine used as reference compound.

The first clinical tests were carried out with topical compositions containing the active ingredient (ointment, cream, solution, tincture, paste, aerosol). Creams containing 2%, 1%, 0.5%, 0.25% and 0.1% of (−)-9-nitro- or (−)-11-nitroapovincaminol-3',4,40 ,5'-trimethoxy-benzoate, respectively, were used.

Patients suffering from psoriasis were treated. A further fundamental point of view of the selection was that the patients did not receive simultaneously a systemic treatment of their basic disease (e.g. an immunosuppressive, cytostatical or glucocorticoidal treatment).

Groups consisting of five patients each were examined, by the so-called plaque method. One side of the symmetrical skin lesions was treated with the cream containing the active ingredient while the other side was treated with a placebo. The other effected skin surfaces of the patient were treated by other topical methods-among others with an ointment generally used for the treatment of psoriasis, containing flumethasone pivalate and salicyclic acid, said oitnment being used as reference substance.

The test had been started with creams having a higher active ingredient content and further patients were treated with a cream having the lowest active ingredient content but being still active. The cream was spread on the skin surface twice or three times a day until the symptoms disappeared or improved (generally 1–6 weeks).

The effect was evaluated by observing three different symptoms—inflammation, infiltration and desquamation (peeling). The intensity of the symptoms was expressed by the following scale between 0 and 3
0 = no symptoms
1 = moderate symptoms
2 = strong symptoms
3 = very strong symtoms The symptoms were evaluated before treatment (I), after a treatment of seven days (II) and after treatment of fourteen days (III). In the following Table the average number of points (total number of points divided by the number of patients) is disclosed. A cream containing 2% active ingredient was used.

| Test compound | Average number of points | | | | | | | | |
|---|---|---|---|---|---|---|---|---|---|
| | Infiltration | | | Inflammation | | | Desquamation | | |
| | I | II | III | I | II | III | I | II | III |
| 9-nitro-compound | 2.2 | 1 | 0.7 | 2.5 | 2.5 | 1.3 | 1.5 | 0.5 | 0 |
| 11-nitro-compound | 2.4 | 1.8 | 1.3 | 2.2 | 1.3 | 1.3 | 1.6 | 1.2 | 0.8 |

The above tests prove unamiguously that the compositions of the present invention can be successfully used in the therapy of psoriasis. During the treatment no undesired side effects were observed.

According to a further feature of the present invention there is a process for the preparation of compounds of the Formulas Ia and Ib and pharmaceutically acceptable acid addition salts thereof which comprises nitrating a compound of the Formula II and isolating the mixture of the compounds of the Formulae Ia and Ib thus obtained or if desired separating the mixture into two components and if desired converting a compound of the Formula Ia or Ib thus obtained into pharmaceutically acceptable acid additions salts thereof.

As starting material the new compound of the Formula II is used which can be prepared by reacting apovincaminol-3,4,5-trimethoxy-benzoic acid or a reactive derivative thereof.

The obtained starting material of the Formula II is nitrated. The reaction is carried out preferably with concentrated nitric acid and advantageously in glacial acetic acid as medium. The nitration is carried out under cooling, preferably at a temperature of about 0° C. The reaction having been completed, the excess of the acid is neutralized and the mixture of the compound of the Formulae Ia and Ib is isolated from the reaction mixture by extraction and/or evaporation.

The isomer mixture may be separated, if desired, into its components. The separation may be carried out preferably by chromatographical methods.

The product thus obtained may be converted into a pharmaceutically acceptable acid addition salt. Salt formation may be carried out by using an inorganic or organic acids (e.g. hydrochloric acid, sulfuric acid or phosphoric acid or tartaric acid, succinic acid, citric acid or ascorbic acid). The salt formation is carried out by methods known per se. One may proceed preferably by adding a solution of the acid in ethyl ether or acetone to the solution of the base. Salt formation is accomplished at a pH value of 3-6.

According to a still further feature of the present invention there are provided pharmaceutical compositions having phosphodiesterase inhibitory effect and being mainly useful in the treatment of skin diseases attached to pathological cell proliferation and the prophylaxis of the recurrence of such diseases the said compositions comprising as active ingredient 9-nitro- and/or 11-nitro-apovincaminol-3',4',5=-trimethoxybenzoate or a pharmaceutically acceptable acid additions salt thereof and optionally further therapeutically active compounds in admixture with usual pharmaceutical carriers and/or diluents.

The active ingredient content of the pharmaceutical compositions of the present invention is preferably 0.1–8.0%, particularly 0.2–2.0%. The compositions may optionally contain further therapeutically active compounds, such as antibiotics, cytostatical agents, prostaglandines, ditranol, salicyclic acid, tar, antiinflammatory agents, immunosupressants, glucocorticoides and—in the case if compositions suitable for parenteral administration—local anaesthetical agents. As glucocorticoid preferably triamcinolon-acetonide may be used. The active ingredient may be finished preferably in the form of compositions for topical use, such as creams, ointments, solutions, gelees, aerosols, aerosol foams, adhesive plasters, etc.

The active ingredient may be preferably used in the form of the base but acid addition salts may be applied as well.

It is preferred to incorporate the active ingredient into a cream, which can be washed off.

The creams may be prepared by dissolving the active ingredient in a solvent of the alcoholic type, preferably in propylene glycol or ethylene glycol or a mixture thereof formed with a small amount of water, and admixing the solution thus obtained with a readily spreadable fatty phase being skin compatible.

The said fatty phase may comprise cetyl alcohol, stearyl alcohol, cetostearyl alcohol, paraffin oil, glycerine monostearate or etc.

The cream may also contain an emulsifying agent—preferably polyoxyethylene sorbitan monooleate or monostearate—and a preservative such as a benzoic acid derivatives, preferably methyl-p-hydroxy benzoate.

The creams may contain preferably 0.25–2.0% of the active ingredient, 45–50% of glycol, 23–27% of paraffin oil, 11–15% of stearyl alcohol and optionally up to 100% other auxiliary agent.

The active ingredient can also be finished in the form of an ointment which can not be washed off with water by incorporating the active ingredient directly in the fatty phase.

The active ingredient can also be finished in the form of a solution or tincture which may contain e.g. 20–40% of propylene glycol or dipropylene glycol, 40–55% of ethanol and up to 100% distilled water.

The aerosol formulations may be prepared by adding to the solution of the active ingredient in propylene glycol a fatty substance—e.g. isopropyl myristate—and a propellant (e.g. freon).

Injectable solutions suitable for parenteral administration preferably applicable in a subcutaneous or intracutaneous route may be prepared by dissolving a salt of the active ingredient in a 0.72% aqueous sodium chloride solution and adjusting the pH of the solution to 5.

The pharmaceutical compositions of the present invention can be prepared by methods known in the pharmaceutical industry known per se. One may proceed by admixing the active ingredient and optionally further therapeutically active compounds with suitable inert non-toxical usual pharmaceutical carriers and/or additives and finishing the mixture thus obtained in a form suitable for medical use.

Further details of the present invention can be found in the following Examples without limiting the scope of the invention in any way.

EXAMPLE 1

Preparation of (−)-9-nitro-apovincaminol-3',4',5'-trimethoxy-benzoate and (−)-11-nitro-apovincaminol-3',4',5'-trimethoxybenzoate 5 g of (−)-apovincaminol-3',4',5'-trimethoxy-benzoate are dissolved in 50 ml of glacial acetic acid. To the solution obtained a mixture of 20 ml of glacial acetic acid and 10 ml of concentrated nitric acid (d=1.52) is added at 0° C. under stirring. The reaction mixture is poured into 350 g of icecold water and the pH is adjusted to 9 by adding a 25% aqueous ammonium hydroxide solution. The alkaline solution is extracted at first with 250 ml and thereafter twice with 200 ml of dichloro methane each. The united organic solutions are dried over anhydrous sodium sulfate, filtered and the filtrate is evaporated to dryness in vacuo.

The isomer mixture thus obtained is prepared into the two components by chromatographical methods by using Kieselgel 60 as adsorbent and a 10:2 mixture of benzene and acetone as developing agent. Under these conditions the $R_f$ value of the 9-nitro compound is greater than that of the 11-nitro derivative. Thus 1.7 g. of the 9-nitrocompound and 1.8 of the 11-nitro-derivative are obtained.

The physical constants of the (−)-9-nitro-apovincaminol-3',4',5'-trimethoxy-benzoate are as follows:
Mp.: 88°–78° C.
$[\alpha]_D = -78.5°$ (c=1, chloroform).
$^1$H-NMR (CDCl$_3$): $\delta$3.8 (s, 6H, 2×CH$_3$O—); $\delta$3.91 (s, 3H, 1×CH$_3$O—); $\delta$7.3 (d, 1H, H$_{12}$); $\delta$7.96 (d, 1H, H$_{11}$); $\delta$8.1 (d, 1H, H$_{10}$).

The physical constants of the (−)-11-nitroapovincaminol-3',4',5'-trimethoxy-benzoate are as follows:
Mp.: 72°–73° C.
$[\alpha]_D = -134.3°$ (c=1, chloroform).
$^1$H-NMR (CDCl$_3$): $\delta$3.8 (s, 6H, 2×CH$_3$O—); $\delta$3.9 (s, 3H, 1×CH$_3$O—); $\delta$7.56 (d, 1H, H$_9$); $\delta$8.1 (d, 1H, H$_{10}$); $\delta$8.9 (d, 1H, H$_{12}$).

The (−)-apovincaminol-3',4',5'-trimethoxy-benzoate used as starting material may be prepared as follows:

3.10 g (10.1 millimoles) of (−)-apovincaminol are dissolved in 60 ml of anhydrous dichloromethane, whereupon 3.10 g of anhydrous sodium carbonate and 2.50 g (10.9 millimoles) of 3,4,5-trimethoxy-benzoyl chloride are added and the reaction mixture is stirred at room temperature for 24 hours. The reaction mixture is diluted with 100 ml of water, the organic phase is separated and the aqueous layer is extracted twice with 20 ml of dichloromethane each. The united dichloromethane phases are dried over magnesium sulfate, filtered and the filtrate is evaporated in vacuo. Thus 4.50 of (−)-apovincaminol-3′,4′,5′-trimethoxy-benzoate are obtained, yield 89.1%.

Brutto formula $C_{30}H_{34}N_2O_5$.

Molecular weight 502.61.

IR spectrum (film): $\nu_{max}$ 1725 cm$^{-1}$ (=C=O); 1620 cm$^{-1}$ (=C=C=).

MS (m/e): 502(53), 432(100), 290(17), 261(41), 220(19), 216(23), 212(18), 195(35).

$[\alpha]_D^{25} = -22.0°$ (c=0.7, dichloro methane).

EXAMPLE 2

Preparation of
9-nitro-apovincaminol-3′,4′,5′-trimethoxy-benzoate-hydrochloride and
11-nitro-apovincaminol-3′,4′,5′-trimethoxy-benzoate-hydrochloride The 9-nitro- or 11-nitro-apovincaminol-3′,4′,5′-trimethoxy-benzoate prepared according to Example 1 is dissolved in methanol and the pH of the solution is adjusted by adding a solution of hydrogen chloride and methanol. The hydrochloride salt formed is precipitated by adding diethyl ether. The salt is filtered off, washed and dried.

EXAMPLE 3

A cream having the following composition is prepared:

| Component | Amount, g |
| --- | --- |
| 9-Nitro-apovincaminol-3′,4′,5′-trimethoxy-benzoate | 2 |
| Propylene glycol | 50 |
| Paraffin oil | 26 |
| Propyethylene glycol | 5 |
| Stearyl alcohol | 15 |
| Glycerol monostearate | 2 |

The active ingredient is dissolved in propylene glycol on a water bath (bath temperature not exceeding 50° C.). The other components are heated until they melt and thereafter cooled to 40°–45° C. under constant stirring. To the melt the solution of the active ingredient is added under stirring and the cream thus obtained is cooled under stirring.

EXAMPLE 4

One proceeds as described in Example 3 except that 11-nitro-apovincaminol-3′,4′,5′-trimethoxy-benzoate is used as active ingredient.

EXAMPLE 5

A cream having the following composition is prepared:

| Component | Amount, g |
| --- | --- |
| 9-Nitro-apovincaminol-3′,4′,5′-trimethoxy-benzoate | 2 |
| Triamcinolon acetonide | 0.1 |
| Glycerol monostearate | 3.0 |
| Polyethylene glycol 400 | 5.0 |
| Stearyl alcohol | 13.0 |
| Paraffin oil | 24.9 |
| Propylene glycol | 53.0 |

One proceeds in an analogous manner to Example 3 except that two active ingredients are dissolved in propylene glycol.

EXAMPLE 6

A tincture solution having the following composition is prepared:

| Component | Amount, % |
| --- | --- |
| 9-nitro-apovincaminol-3′,4′,5′-trimethoxy-benzoate | 1 |
| Propylene glycol | 30 |
| 96% ethanol | 69 |

EXAMPLE 7

An aerosol having the following composition is prepared:

| Component | Amount, % |
| --- | --- |
| 9-nitro-apovincaminol-3′,4′,5′-trimethoxy-benzoate | 0.5 |
| Propylene glycol | 30.0 |
| Isopropyl myristate | 4.5 |
| Freon | 65.0 |

What we claim is:

1. (−)-9-nitro-apovincaminol-3′,4′,5′-trimethoxy-benzoate of the Formula Ia

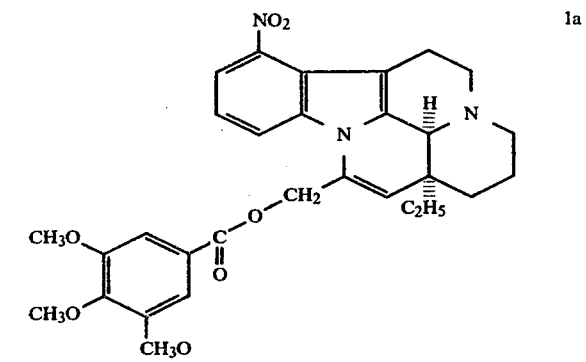

or a pharmaceutically acceptable acid addition salt thereof.

2. (−)-11-nitro-apovincaminol-3′,4′,5′-trimethoxy-benzoate of the Formula Ib

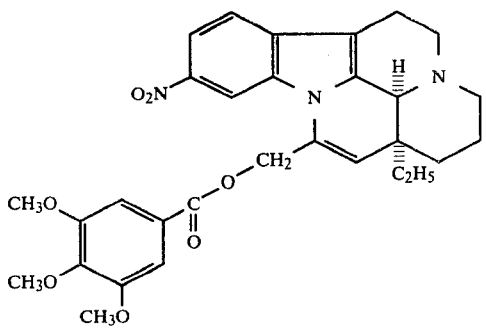

or a pharmaceutically acceptable acid addition salt thereof.

3. A pharmaceutical composition for the treatment of psoriasis and for the prophylaxis of the recurrence of such disease which comprises as active ingredient an effective amount of (—)-9-nitro-apovincaminol-3',4',5'-trimethoxy-benzoate as defined in claim 1 or a pharmaceutically acceptable acid addition salt thereof in admixture with a pharmaceutically acceptable inert carrier.

4. The pharmaceutical composition defined in claim 3 which comprises 0.1 to 8.0% of the (—)-9-nitro-apovincaminol-3',4',5'-trimethoxy-benzoate or a pharmaceutically acceptable acid addition salt thereof.

5. The pharmaceutical composition defined in claim 3 in the form of a cream, ointment, solution, aerosol, aerosol foam, or an injection suitable for subcutaneous or intracutaneous administration.

6. A method for the treatment and prophylaxis of psoriasis which comprises the step of treating the affected skin surface with a pharmaceutically effective amount of the (—)-9-nitro-apovincaminol-3',4',5'-trimethoxy-benzoate or a pharmaceutically acceptable salt thereof, as defined in claim 1.

7. A pharmaceutical composition for the treatment of psoriasis and for the prophylaxis of the recurrence of such disease which comprises as active ingredient an effective amount of (—)-11-nitro-apovincaminol-3',4',5'-trimethoxy-benzoate as defined in claim 2 or a pharmaceutical acceptable acid addition salt thereof in admixture with a pharmaceutically acceptable inert carrier.

8. The pharmaceutical composition defined in claim 7 which comprises 0.1 to 8.0% of the (—)-11-nitro-apovincaminol-3',4',5'-trimethoxy-benzoate or a pharmaceutically acceptable acid addition salt thereof.

9. The pharmaceutical composition defined in claim 7 in the form of a cream, ointment, solution, aerosol, aerosol foam, or an injection suitable for subcutaneous or intracutaneous administration.

10. A method for the treatment and prophylaxis of psoriasis which comprises the step of treating the affected skin surface with a pharmaceutically effective amount of the (—)-11-nitro-apovincaminol-3',4',5'-trimethoxy-benzoate or a pharmaceutically acceptable salt thereof, as defined in claim 2.

* * * * *